United States Patent [19]

Takaya et al.

[11] Patent Number: 4,631,274
[45] Date of Patent: Dec. 23, 1986

[54] HALOVINYL CEPHEM COMPOUNDS

[75] Inventors: Takao Takaya; Kazuo Sakane, both of Kawanishi; Hideaki Yamanaka, Hirakata; Kenzi Miyai, Kawanishi, all of Japan

[73] Assignee: Fujisawa Pharmceutical Co., Ltd., Osaka, Japan

[21] Appl. No.: 704,776

[22] Filed: Feb. 25, 1985

[30] Foreign Application Priority Data

Mar. 9, 1984 [GB] United Kingdom ............... 8406231

[51] Int. Cl.⁴ .................. A61K 31/545; C07D 501/24
[52] U.S. Cl. .................................... 514/202; 514/200; 540/215; 540/222; 540/225; 540/227
[58] Field of Search ...................... 544/16, 22, 25, 27; 514/202, 200

[56] References Cited

U.S. PATENT DOCUMENTS 4,065,620  12/1977  Webber ................. 544/16
4,092,477   5/1978  Cook ................... 544/26
4,452,851   6/1984  Takaya ................. 544/16
4,489,072  12/1984  Sadaki ................. 544/22

FOREIGN PATENT DOCUMENTS 0053538  6/1982  European Pat. Off. ........... 544/22

OTHER PUBLICATIONS

Dunn, J. of Antimicrobial Chemotherapy (1982) 10, Suppl. Co. 1-10.

*Primary Examiner*—Sidney Marantz
*Assistant Examiner*—Robert Benson
*Attorney, Agent, or Firm*—Oblon, Fisher, Spivak, McClelland & Maier

[57]   ABSTRACT

The invention relates to novel halovinyl cephem derivatives of high antimicrobial activity of the formula:

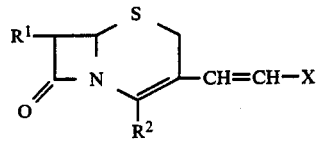

wherein $R^1$ is a group of the formula:

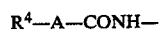

in which $R^4$ is cyano(lower)alkenylthio or a group of the formula:

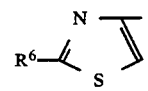

in which
$R^6$ is hydrogen, amino or a protected amino group, and
A is carbonyl, lower alkylene, hydroxy(lower)alkylene or a group of the formula:

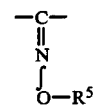

in which
$R^5$ is hydrogen, carboxy(lower)alkyl or protected carboxy(lower)alkyl;
$R^2$ is carboxy or a protected carboxy group; and
X is halogen, and pharmaceutically acceptable salts thereof.

3 Claims, No Drawings

HALOVINYL CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compound and pharmaceutically acceptable salts thereof.

Still further object of the present invention is to provide a method for the treatment of infectious diseases caused by pathogenic bacteria in human being and animals.

The object new cephem compounds are novel and can be represented by the following general formula:

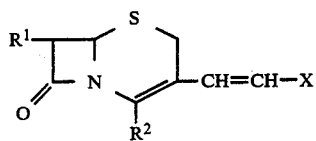

(I)

wherein
R$^1$ is amino or a protected amino group,
R$^2$ is carboxy or a protected carboxy group, and
X is halogen.

According to the present invention, the new cephem compounds (I) can be prepared by processes which are illustrated in the following schemes.

Process 1

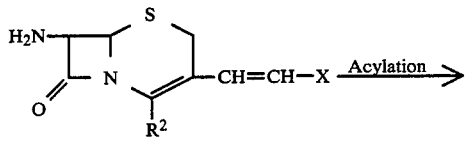

(Ia)
or its reactive derivative at the amino group or a salt thereof

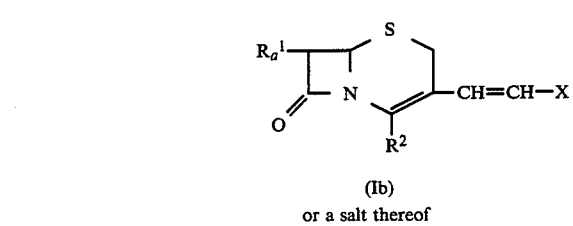

(Ib)
or a salt thereof

Process 2

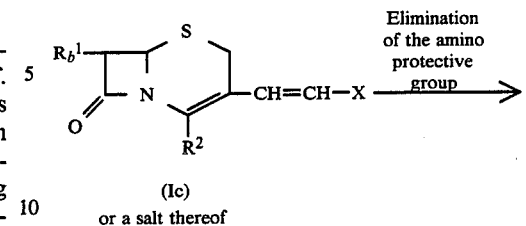

(Ic)
or a salt thereof

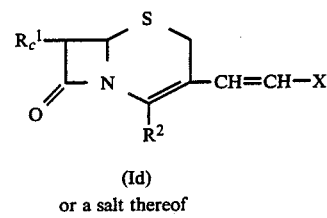

(Id)
or a salt thereof

Process 3

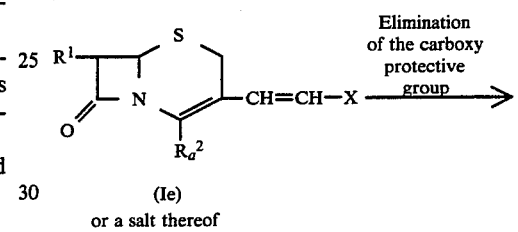

(Ie)
or a salt thereof

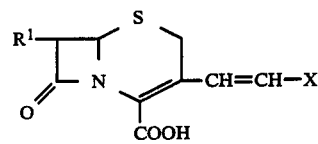

(If)
or a salt thereof

Process 4

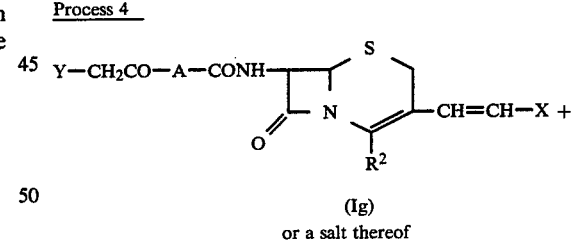

(Ig)
or a salt thereof

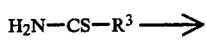

$$H_2N-CS-R^3 \longrightarrow$$
(II)

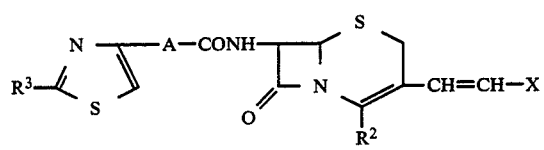

(Ih)
or a salt thereof

Process 5

-continued

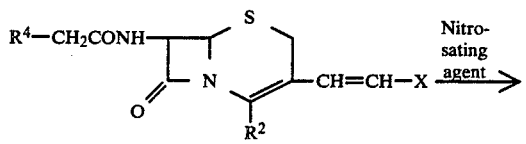

(Ii)
or a salt thereof

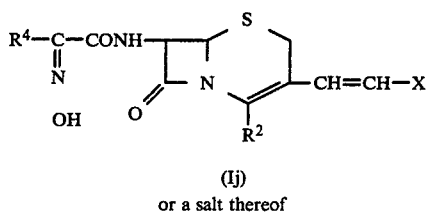

(Ij)
or a salt thereof

Process 6

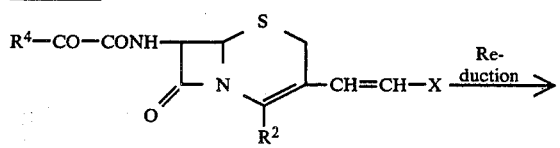

(Ik)
or a salt thereof

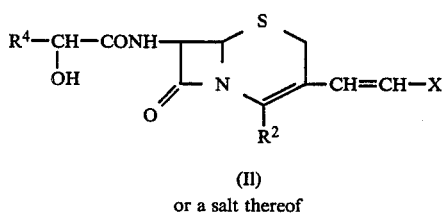

(Il)
or a salt thereof

Process 7

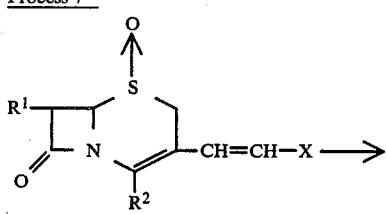

(III)
or a salt thereof

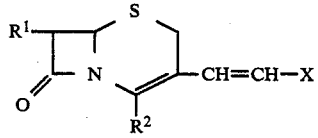

(I)
or a salt thereof

Process 8

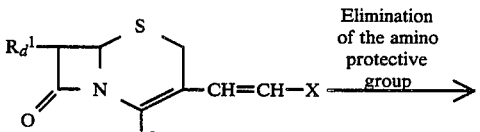

(Im)
or a salt thereof

-continued

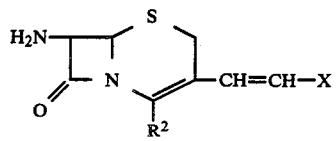

(Ia)
or a salt thereof wherein
$R^1$, $R^2$ and X are each as defined above;
$R_a^1$ is acylamino;
$R_b^1$ is acylamino having protected amino group;
$R_c^1$ is acylamino having amino group;
$R_a^2$ is a protected carboxy group;
Y is an acid residue;
A is carbonyl, lower alkylene, hydroxy(lower)alkylene or a group of the formula:

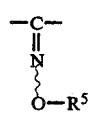

in which
$R^5$ is hydrogen or an organic group which may have suitable substituent(s);
$R^3$ is amino or a protected amino group;
$R^4$ is halo(lower)alkanoyl, cyano(lower)alkenylthio, aryl or a group of the formula:

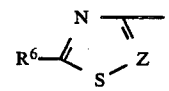

in which
$R^6$ is hydrogen, amino or a protected amino group and Z is N or CH; and
$R_d^1$ is a protected amino group.

The preferable compounds among the object new cephem compounds (I) are the compounds of the following general formula (I'):

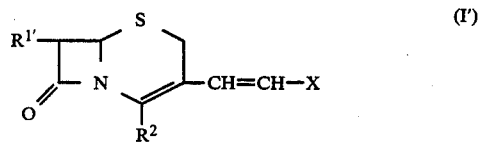

wherein
$R^2$ and X are each as defined above, and
$R^{1'}$ is amino, lower alkoxycarbonylamino or a group of the formula:

$R^4$—A—CONH— in which $R^4$ and A are each as defined above.

Suitable pharmaceutically acceptable salts of the object compound (I) are conventional non-toxic salts and may include an inorganic salt, for example, a metal salt such as an alkali metal salt (e.g. sodium salt, potassium salt, etc.) and an alkaline earth metal salt (e.g., calcium salt, magnesium salt, etc.), ammonium salt etc.; an organic salt, for example, an organic amine salt (e.g., trimethylamine salt, triethylamine salt, pyridine salt, procaine salt, picoline salt, dicyclohexylamine salt, N,N'-dibenzylethylene-diamine salt, N-methylglucamine salt, diethanolamine salt, triethanolamine salt, tris(hydroxymethylamino)methane salt, phenylethylbenzylamine salt, dibenzylethylenediamine salt, etc.) etc.; an organic carboxylic or sulfonic acid salt (e.g., formate, acetate, maleate, tartrate, methanesulfonate, benzenesulfonate, toluenesulfonate, etc.); an inorganic acid salt (e.g., hydrochloride, hydrobromide, sulfate, phosphate, etc.); a salt with a basic or acidic amino acid (e.g., arginine, aspartic acid, glutamic acid, lysine, etc.) and the like.

In the above and subsequent descriptions of the present specification, suitable examples and illustration of the various definitions which the present invention intends to include within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated.

Suitable "protected amino" may include acylamino; phosphonoamino; protected phosphonoamino; ar(-lower)alkylamino such as benzylamino, phenethylamino, tritylamino; ar(lower)alkylideneamino which may have hydroxy such as benzylideneamino, hydroxybenzylideneamino, phenethylideneamino; and the like.

Suitable "acyl" moiety in the terms "acylamino", "acylamino having protected amino group" and "acylamino having amino group" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Aliphatic acyl such as lower or higher alkanoyl (e.g. formyl, acetyl, propionyl, butyryl, succinyl, hexanoyl, heptanoyl, valeryl, stearoyl, etc.); lower or higher alkoxycarbonyl (e.g. methoxycarbonyl, ethoxycarbonyl, t-butoxycarbonyl, t-pentyloxycarbonyl, heptyloxycarbonyl, etc.); lower or higher alkanesulfonyl (e.g. methanesulfonyl, ethanesulfonyl, etc.); lower or higher alkoxysulfonyl, (e.g. methoxysulfonyl, ethoxysulfonyl, etc.); or the like;

Aromatic acyl such as aroyl (e.g. benzoyl, toluoyl, naphthoyl, etc.); ar(lower)alkanoyl such as phenyl(lower)alkanoyl (e.g. phenylacetyl, phenylpropionyl, etc.); aryloxycarbonyl (e.g. phenoxycarbonyl, naphthyloxycarbonyl, etc.); aryloxy(lower)alkanoyl (e.g. phenoxyacetyl, phenoxypropionyl, etc.); arylglyoxyloyl (e.g. phenylglyoxyloyl, naphthylglyoxyloyl, etc.); arenesulfonyl (e.g. benzenesulfonyl, p-toluenesulfonyl, etc.); or the like;

Heterocyclic acyl such as heterocycliccarbonyl (e.g. thenoyl, furoyl, nicotinoyl, etc.); heterocyclic(lower)alkanoyl (e.g. thienylacetyl, thiazolylacetyl, thiadiazolylacetyl, tetrazolylacetyl, etc.); heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; saturated 3 to 8-membered (more preferably 5 or 6-membered) heteromonocyclic group containing 1 to 4 nitrogen atom(s), for example pyrrolidinyl, imidazolidinyl, piperidino, piperazinyl, etc.; unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.; unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.; saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.; saturated 3 to 8-membered (more preferably 5 or 6-membered) heteromonocyclic group containing 1 to 2 sulfur atom(s) and 1 to 3 nitrogen atom(s), for example, thiazolidinyl, etc.; unsaturated 3 to 8-membered (more preferably 5 or 6-membered) heteromonocyclic group containing 1 to 2 sulfur atom(s), for example, thienyl, dihydrodithiinyl, dihydrodithiolyl, etc.; unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered (more preferably 5 to 6-membered) heteromonocyclic group containing an oxygen atom, for example, furyl, etc.; unsaturated 3 to 8-membered (more preferably 5 or 6-membered) heteromonocyclic group containing an oxygen atom and 1 to 2 sulfur atom(s), for example, dihydrooxathiinyl, etc.; unsaturated condensed heterocyclic group containing 1 to 2 sulfur atom(s), for example, benzothienyl, benzodithiinyl, etc.; unsaturated condensed heterocyclic group containing an oxygen atom and 1 to 2 sulfur atom(s), for example, benzoxathiinyl, etc. and the like.

The acyl moiety as stated above may have one to ten, same or different, suitable substituent(s) such as lower alkyl (e.g. methyl, ethyl, etc.); lower alkoxy (e.g. methoxy, ethoxy, propoxy, etc.); lower alkylthio (e.g. methylthio, ethylthio, etc.); lower alkylamino (e.g. methylamino, etc.); cyclo(lower)alkyl (e.g. cyclopentyl, cyclohexyl, etc.); cyclo(lower)alkenyl (e.g. cyclohexenyl, cyclohexadienyl, etc.); halogen; amino; protected amino; hydroxy; protected hydroxy; cyano; nitro; carboxy; protected carboxy; sulfo; sulfamoyl; imino; oxo; amino(lower)alkyl (e.g. aminomethyl, aminoethyl, etc.); carbamoyloxy; cyano(lower)alkenylthio (e.g. cyanovinyl)thio, etc.); a group of the formula: $=N-OR^5$, wherein $R^5$ is as defined above, or the like. In this connection, when the acyl moiety has a group of the formula: $=N-OR^5$, wherein $R^5$ is as defined above, as substituent(s), there are geometrical isomers (syn and anti isomers) due to the presence of double bond. And, for example, the syn isomer means one geometrical isomer having the group of the formula:

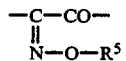

and the corresponding anti isomer means the other geometrical isomer having the group of the formula:

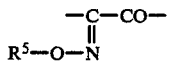

Suitable "protected carboxy" may include an esterified carboxy and the like.

Suitable examples of the ester moiety in said esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester [e.g., mono(or di or tri)phenyl(lower)alkyl ester, etc.], which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.), and the like.

Suitable "halogen" may include chlorine, bromine, fluorine and iodine.

Suitable "protected amino moiety" in the term "acylamino having protected amino group" can be referred to the ones as mentioned above.

Suitable "acid residue" may include halogen (e.g. fluorine, chlorine, bromine or iodine) and the like.

Suitable "lower alkylene" and "lower alkylene moiety" in the term "hydroxy(lower)alkylene" may include methylene, ethylene, trimethylene, tetramethylene and the like.

Suitable "organic group which may have suitable substituent(s)" may include lower alkyl (e.g. methyl, ethyl, propyl, isopropyl, butyl, isobutyl, t-butyl, pentyl, hexyl, etc.), lower alkenyl (e.g. vinyl, allyl, butenyl, pentenyl, hexenyl, etc.), lower alkynyl (e.g. ethynyl, propynyl, etc.), cyclo(lower)alkyl (e.g. cyclopropyl, cyclohexyl, etc.), ar(lower)alkyl such as phenyl(lower)alkyl (e.g. benzyl, phenethyl, etc.), carboxy(lower)alkyl (e.g. carboxymethyl, 1-carboxyethyl, carboxypropyl, etc.), protected carboxy(lower)alkyl (e.g. esterified carboxy(lower)alkyl wherein the esterified carboxy is as exemplified above, etc.), hydroxy(lower)alkyl (e.g. hydroxymethyl, hydroxyethyl, etc.), carboxy(lower)alkenyl (e.g. carboxyvinyl, carboxyallyl, carboxy-2-butenyl, etc.), protected carboxy(lower)alkenyl, cyclo(lower)alkenyl (e.g. cyclobutenyl, cyclopentenyl, cyclohexenyl, etc.), saturated 4 to 8-membered heteromonocyclic group containing one sulfur atom (e.g. thietanyl, thiolanyl, thianyl, thiepanyl, thiocanyl, etc.), and the like.

Suitable "halo(lower)alkanoyl" may include chloroacetyl, bromoacetyl, fluoroacetyl, iodoacetyl, chloropropionyl, bromopropionyl, fluoropropionyl, iodopropionyl and the like.

Suitable "cyano(lower)alkenylthio" may include cyanovinylthio, cyanoallylthio, cyanobutenylthio, cyanopentenylthio, cyanohexenylthio and the like.

Suitable "aryl" may include phenyl, tolyl, naphtyl and the like.

Suitable "lower alkoxycarbonylamino" may include methoxycarbonylamino, ethoxycarbonylamino, propoxycarbonylamino, isopropoxycarbonylamino, butoxycarbonylamino, isobutoxycarbonylamino, t-butoxycarbonylamino, pentyloxycarbonylamino, hexyloxycarbonylamino and the like.

Preferable embodiments of the object compounds (I') are as follows.

Preferred embodiment of $R^{1'}$ is amino; lower alkoxycarbonylamino or a group of the formula: $R^4$—A—CONH— in which $R^4$ is halo(lower)alkanoyl, cyano(lower)alkenylthio [more preferably cyanovinylthio], aryl (more preferably phenyl) or a group of the formula:

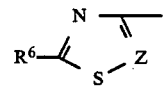

in which $R^6$ is hydrogen, amino or a protected amino group (more preferably acylamino, most preferably lower alkanoylamino) and Z is N or CH, and A is carbonyl, lower alkylene (more preferably methylene), hydroxy(lower)alkylene (more preferably hydroxymethylene) or a group of the formula:

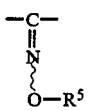

9 in which
  $R^5$ is hydrogen, lower alkyl, carboxy(lower)alkyl or protected carboxy(lower)alkyl [more preferably esterified carboxy(lower)alkyl, most preferably lower alkoxycarbonyl(lower)alkyl],
  $R^2$ is carboxy or protected carboxy (more preferably esterified carboxy, most preferably mono(or di or tri)phenyl(lower)alkoxycarbonyl], and
  X is halogen (more preferably chlorine)

The processes for preparing the object compounds of the present invention are explained in detail in the following.

Process 1

The object compound (Ib) or a salt thereof can be prepared by subjecting the compound (Ia) or its reactive derivative at the amino group or a salt thereof to acylation reaction.

Suitable reactive derivative at the amino group of the compound (Ia) may include Schiff's base type imino or its tautomeric enamine type isomer formed by the reaction of the compound (Ia) with a carbonyl compound such as aldehyde, ketone or the like; a silyl derivative formed by the reaction of the compound (Ia) with a silyl compound such as bis(trimethylsilyl)acetamide, trimethylsilylacetamide, bis(trimethylsilyl)urea or the like; a derivative formed by reaction of the compound (Ia) with phosphorus trichloride or phosgene, and the like.

Suitable acylating agent to be used in the present acylation reaction may include conventional one and can be shown by the formula:

$R^7$—OH  (IV)

(wherein $R^7$ is acyl) or its reactive derivative or a salt thereof.

Suitable salts of the compounds (Ia), (Ib) and (IV) can be referred to the ones as exemplified for the compound (I).

Suitable reactive derivative of the compound (IV) may include an acid halide, an acid anhydride, an activated amide, an activated ester, and the like. The suitable example may be an acid chloride, an acid bromide; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, lower alkanesulfonic acid (e.g. methanesulfonic acid, ethanesulfonic acid, etc.), sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (IV) to be used.

The reaction is usually carried out in a conventional solvent such as water, methanol, ethanol, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

When the compound (IV) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like. The reaction temperature is not critical, and the reaction is usually carried out under cooling or at ambient temperature.

Process 2

The object compound (Id) or a salt thereof can be prepared by subjecting the compound (Ic) or a salt thereof to elimination reaction of the amino protective group.

Suitable salts of the compounds (Ic) and (Id) can be referred to the ones as exemplified for the compound (I).

The present elimination reaction is carried out in accordance with a conventional method such as hydrolysis; reduction; a method by reacting the compound (Ic) wherein the protective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarbonyl, t-butoxycarbonyl, etc.), alkanoyl (e.g. formyl, etc.), cycloalkoxycarbonyl, substituted or unsubstituted aralkoxycarbonyl (e.g. benzyloxycarbonyl, substituted benzyloxycarbonyl, etc.), ar(lower)alkyl (e.g. benzyl, trityl, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent (e.g. methanol, ethanol, acetonitrile, tetrahydrofuran, etc.), water or a mixture thereof. When trifluoroacetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g. dichloroacetyl, trifluoroacetyl, etc.), etc. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. megnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4.3.0]non-5-ene, 1,4-diazabicyclo[2.2.2]octane, 1,8-diazabicyclo[5.4.0.]undecene-7 or the like. The hydrolysis using a base is often carried out in water, a conventional organic solvent or a mixture thereof.

Among the protective group, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g. sodium borohydride, etc.) and the like.

The reaction temperature is not critical and may be suitable selected in accordance with the kind of the protective group of the amino group and the elimination method as mentioned above, and the present reaction is preferably carried out under a mild condition such as under cooling, at ambient temperature or slightly elevated temperature.

Process 3

The object compound (If) or a salt thereof can be prepared by subjecting the compound (Ie) or a salt thereof to elimination reaction of the carboxy protective group.

Suitable salts of the compounds (Ie) and (If) can be referred to the ones as exemplified for the compound (I).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4.3.0]-none-5-ene, 1,4-diazabicyclo[2.2.2]octane, 1,8-diazabicyclo[5.4.0]undecene-7, or the like. Suitable acid may include formic acid, acetic acid, propionic acid, trifluoroacetic acid, hydrochloric acid, hydrobromic acid, sulfuric acid, boron trifluoride and the like.

The reaction is usually carried out in a solvent such as water, methylene chloride, an alcohol (e.g. methanol, ethanol, etc.), a mixture thereof or any other solvent which does not adversely influence the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like.

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction is usually carried out in a solvent such as water, alcohol (e.g. methanol, ethanol, etc.) N,N-dimethylformamide, tetrahydrofuran, a mixture thereof or any other solvent which does not adversely affect the reaction. Additionally, in case that the above-mentioned acids to be used in chemical reduction are in liquid, they can also be used as a solvent.

The reaction temperature of this reduction is not critical and the reaction is usually carried out under cooling to warming.

The present invention includes, within its scope, the case that another protected carboxy group is converted into the corresponding free carboxy group during the reaction or the post-treating step of the present process.

Process 4

The object compound (Ih) or a salt thereof can be prepared by reacting the compound (Ig) or a salt thereof with the compound (II).

Suitable salts of the compounds (Ig) and (Ih) can be referred to the ones as exemplified for the compound (I).

The present reaction is usually carried out in a solvent such as water, an alcohol (e.g. methanol, ethanol, etc.), benzene, N,N-dimethylformamide, N,N-dimethylacetamide, methylene chloride, ethyl acetate, tetrahydrofuran or any other solvent which does not adversely influence the reaction.

The reaction temperature is not critical and the reaction is usually carried out from at ambient temperature to under heating.

Process 5

The object compound (Ij) can be prepared by reacting the compound (Ii) or a salt thereof with a nitrosating agent.

Suitable nitrosating agent may include nitrous acid, alkali metal nitrite (e.g. sodium nitrite, etc.), lower alkyl nitrite (e.g. amyl nitrite, etc.) and the like.

The present reaction is usually carried out in a solvent such as water, acetic acid, benzene, methanol, ethanol, methylene chloride or any other solvent which does not adversely influence the reaction.

The reaction temperature is not critical and the reaction is usually carried out under cooling or at ambient temperature.

Process 6

The object compound (II) or a salt thereof can be prepared by reducing the compound (Ik) or a salt thereof.

Suitable salts of the compounds (Ik) and (II) can be referred to the ones as exemplified for the compound (I).

The present reduction is conducted by a conventional method such as a method of using an alkali metal borohydride (e.g. sodium borohydride, potassium borohydride, etc.) or the like.

The present reduction is usually carried out in a solvent which does not adversely influence the reaction, for example, water, methanol, ethanol, tetrahydrofuran, dioxane and the like. The present reduction can also be carried out in the presence of an inorganic or an organic base such as an alkali metal (e.g. sodium, potassium, etc.), an alkaline earth metal (e.g. magnesium, calcium, etc.), the hydroxide or carbonate or bicarbonate thereof, tri(lower)alkylamine (e.g. trimethylamine, triethylamine, etc.), picoline, N-methylpyrrolidine, N-methylmorpholine, 1,5-diazabicylo[4.3.0]none-5-ene, 1,4-diazabicyclo[2.2.2]octane, 1,8-diazabicyclo[5.4.0]-undecene-7, or the like.

The reaction temperature is not critical and the present reaction is preferably carried out under a mild condition such as under cooling or slightly warming.

Process 7

The object compound (I) or a salt thereof can be prepared by reducing the compound (III) or a salt thereof.

Suitable salts of the compound (II) can be referred to the ones as exemplified for the compound (I).

The present reduction can be carried out by a conventional method which is applied for the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present reduction is usually carried out in a solvent such as acetone, dioxane, acetonitrile, N,N-dimethylformamide, benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

Process 8

The object compound (Ia) or a salt thereof can be prepared by subjecting the compound (Im) or a salt thereof to elimination reaction of the amino protective group. Suitable salts of the compound (Im) can be referred to the ones as exemplified for the compound (I). The present elimination reaction can be carried out in a similar manner to that of Process 2.

The object compound (I) and pharmaceutically acceptable salt thereof of the present invention are novel compounds which exhibit high antibacterial activity and inhibit the growth of a wide variety of pathogenic microorganisms including Gram-positive and Gram-negative bacteria and are useful as anti-microbial agents, especially for oral administration. For therapeutic purpose, the compounds according to the present invention can be used in the form of pharmaceutical preparation which contain said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, ointments or suppositories, solution, suspension, emulsions, and the like. If desired, there may be included in the above preparations auxiliary substances, stabilizing agents, wetting or emulsifying agents, buffers and other commonly used additives.

While the dosage of the compounds will vary dependent upon the age and condition of the patient, an average single dose of about 10 mg., 50 mg., 100 mg., 250 mg., 500 mg., and 1000 mg. of the compounds according to the present invention may be effective for treating infectious diseases caused by pathogenic bacteria. In general, amounts between 1 mg/body and about 6,000 mg/body or even more may be administered per day.

In order to illustrate the usefulness of the object compound, anti-microbial activities, urinary excretion and biliary excretion of a representative compound of the present invention are shown below.

[1] Test Compound

7-[2-Carboxymethoxyimino-2-(2-aminothiazol-4-yl)acetamido]-3-[(E)-2-chlorovinyl]-3-cephem-4-carboxylic acid (syn isomer) (hereinafter referred to as compound Ⓐ).

[2] Test (A) Minimal inhibitory concentrations

① Test Method

In vitro antibacterial activity was determined by the two-fold agar-plate dilution method as described below. One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

① Test Results

| | MIC (μg/ml) |
|---|---|
| Test strains | Compound Ⓐ |
| *Proteus mirabilis* 18 | <0.025 |
| *Proteus vulgaris* 2 | <0.025 |

(B) Urinary excretion

1 Test Method

Urine of rats was collected with a urine collector at 0 to 6, and 6 to 24 hours after oral administration of 20 mg/kg of the test antibiotic. The antibiotic levels in the urine samples were bioassayed with the standard solution prepared with M/15 phosphate buffer (pH 7.0) and the urinary recovery in 24 hours was calculated.

② Test Result

| | Urinary recovery in 24 hours (%) |
|---|---|
| Compound Ⓐ | 51.11 |

(C) Biliary excretion

① Test Method

Rats anesthetized with pentobarbital were fixed in supine position, and a polyethylene cannula was inserted into the bile duct. Bile samples were collected at 0 to 3, 3 to 6, and 6 to 24 hours after oral administration of 20 mg/kg of the test antibiotic. The antibiotic levels in the bile samples were bioassayed with the standard solution prepared with M/15 phosphate buffer (pH 7.0) and the biliary recovery in 24 hours were calculated.

② Test Result

| | Biliary recovery in 24 hours (%) |
|---|---|
| Compound Ⓐ | 24.25 |

The following Examples are given for the purpose of illustrating the present invention.

EXAMPLE 1

Vilsmeier reagent prepared from N,N-dimethylformamide (0.50 g) and phosphorus oxychloride (1.04 g) was suspended in dry tetrahydrofuran (15 ml). To the suspension was added 2-t-butoxycarbonylmethoxyimino-2-(2-formamidothiazol-4-yl)acetic acid (syn isomer) (1.87 g) and the mixture was stirred for an hour at 5° C. to give an activated acid solution.

To a solution of benzhydryl 7-amino-3-[(E)-2-chlorovinyl]-3-cephem-4-carboxylate (2.2 g) and trimethylsilylacetamide (2.7 g) in ethyl acetate (20 ml) was added the activated acid solution at −10° C. The reaction mixture was stirred at −10° to −15° C. for half an hour, poured into water and extracted with ethyl acetate. The extract was washed with an aqueous solution of sodium bicarbonate and a saturated aqueous solution of sodium chloride and dried over magnesium sulfate. The solvent was evaporated under reduced pressure and the residue was triturated with diisopropyl ether and collected by filtration to give benzhydryl 7-[2-t-butoxycarbonylmethoxyimino-2-(2-formamidothiazol-4-yl)acetamido]-3-[(E)-2-chlorovinyl]-3-cephem-4-carboxylate (syn isomer) (3.1 g).

IR (Nujol): 3150, 1785, 1720, 1680, 1540 cm$^{-1}$.

NMR (DMSO-d$_6$, δ): 1.38 (9H, s), 3.73 (2H, broad s), 4.57 (2H, s), 5.25 (1H, d, J=5 Hz), 5.93 (1H, dd, J=5 Hz, 8 Hz), 6.93 (1H, s), 6.90–7.60 (13H, m), 8.48 (1H, s), 9.65 (1H, d, J=8 Hz).

EXAMPLE 2

To a suspension of phosphorus pentachloride (0.51 g) in methylene chloride (5 ml) was added 2-methoxyimino-2-(5-amino-1,2,4-thiadiazol-3-yl)acetic acid (syn isomer) (0.46 g) with stirring at −25° C.

The mixture was stirred at −10° to −15° C. for an hour. Then dry diisopropyl ether was added to the solution. The resultant precipitates were collected by filtration and washed with dry diisopropyl ether. To a solution of benzhydryl 7-amino-3-[(E)-2-chlorovinyl]-3-cephem-4-carboxylate (0.7 g) and trimethylsilylacetamide (1.1 g) in ethyl acetate (10 ml) were added the precipitates obtained above at −20° C. with stirring. The reaction mixture was stirred at −15° to −20° C. for an hour. The reaction mixture was poured into water and extracted with ethyl acetate. The extract was washed with 5% aqueous solution of sodium bicarbonate and a saturated aqueous solution of sodium chloride and dried over magnesium sulfate. The solvent was evaporated under reduced pressure and the residue was triturated with diisopropyl ether and collected by filtration to give benzhydryl 7-[2-methoxyimino-2-(5-amino-1,2,4-thiadiazol-3-yl)acetamido]-3-[(E)-2-chlorovinyl]-3-cephem-4-carboxylate (syn isomer) (0.75 g).

IR (Nujol): 3300, 1770, 1720, 1670, 1610 cm$^{-1}$.

NMR (DMSO-d$_6$, δ): 3.79 (2H, ABq, J=18 Hz), 3.93 (3H, s), 5.27 (1H, d, J=5 Hz), 5.96 (1H, dd, J=5 Hz, 8 Hz), 7.0 (1H, s), 7.0–7.67 (12H, m), 8.17 (2H, broad s), 9.69 (1H, d, J=8 Hz).

EXAMPLE 3

To a solution of diketene (1.01 g) in methylene chloride (15 ml) was dropwise added bromine (1.53 g) at −20° C., and the mixture was stirred at the same temperature for 20 minutes and added to a solution of benzhydryl 7-amino-3-[(E)-2-chlorovinyl]-3-cephem-4-carboxylate (3.42 g) and trimethylsilylacetamide (5.3 g) in ethyl acetate (40 ml) at the same temperature. The reaction mixture was stirred at −10° to −15° C. for 10 minutes, poured into water and extracted with ethyl acetate. The extract was washed with 10% aqueous solution of sodium chloride and dried over magnesium sulfate. The solvent was evaporated under reduced pressure and the residue was triturated with diisopropyl ether and collected by filtration to give benzhydryl 7-(4-bromo-3-oxobutyramido)-3-[(E)-2-chlorovinyl]-3-cephem-4-carboxylate (4.8 g).

IR (Nujol): 3300, 1775, 1720, 1660, 1530 cm$^{-1}$.

NMR (DMSO-$d_6$, δ): 3.67 (2H, s), 3.80 (2H, ABq, J=18 Hz), 4.43 (2H, s), 5.23 (1H, d, J=5 Hz), 5.82 (1H, dd, J=5 Hz, 8 Hz), 7.0 (1H, s), 7.17–7.67 (10H, m), 9.13 (1H, d, J=8 Hz).

EXAMPLE 4

To a solution of benzhydryl 7-amino-3-[(E)-2-chlorovinyl]-3-cephem-4-carboxylate (0.7 g) in tetrahydrofuran (15 ml) was added anhydro-O-carboxymandelic acid (0.32 g) under ice-cooling. The mixture was stirred for 3 hours at the same temperature, poured into ethyl acetate, washed with 5% aqueous solution of sodium bicarbonate and water and dried over magnesium sulfate. The solvent was evaporated under reduced pressure to give benzhydryl 7-[D-2-hydroxy-2-phenylacetamido]-3-[(E)-2-chlorovinyl]-3-cephem-4-carboxylate (0.81 g).

IR (Nujol): 3350, 1780, 1720, 1675, 1560, 1510 cm$^{-1}$.

NMR (DMSO-$d_6$, δ): 3.77 (2H, ABq, J=18 Hz), 5.16 (1H, d, J=6 Hz), 5.17 (1H, d, J=5 Hz), 5.83 (1H, dd, J=5 Hz, 8 Hz), 6.19 (1H, d, J=6 Hz), 7.0 (1H, s), 7.0–7.67 (17H, m), 8.87 (1H, d, J=8 Hz).

EXAMPLE 5

The following compounds were obtained according to similar manners to those of Examples 1–4.

(1) Benzhydryl 7-[2-t-butoxycarbonylmethoxyimino-2-(2-aminothiazol-4-yl)acetamido]-3-[(E)-2-chlorovinyl]-3-cephem-4-carboxylate (syn isomer)

IR (Nujol): 3250, 1780, 1720, 1680, 1610, 1530 cm$^{-1}$.

(2) 7-[2-Carboxymethoxyimino-2-(2-aminothiazol-4-yl)acetamido]-3-[(E)-2-chlorovinyl]-3-cephem-4-carboxylic acid (syn isomer).

IR (Nujol): 3250, 1770, 1670, 1630, 1560 cm$^{-1}$.

(3) 7-[2-Methoxyimino-2-(2-aminothiazol-4-yl)acetamido]-3-[(E)-2-chlorovinyl]-3-cephem-4-carboxylic acid (syn isomer)

IR (Nujol): 3270, 1770, 1670, 1550 (broad) cm$^{-1}$.

(4) 7-[2-Hydroxyimino-2-(2-aminothiazol-4-yl)acetamido]-3-[(E)-2-chlorovinyl]-3-cephem-4-carboxylic acid (syn isomer)

IR (Nujol): 3300, 1760, 1670(s), 1635, 1560 cm$^{-1}$.

(5) Benzhydryl 7-[2-methoxycarbonylmethoxyimino-2-(2-aminothiazol-4-yl)acetamido]-3-[(E)-2-chlorovinyl]-3-cephem-4-carboxylate (syn isomer)

IR (Nujol): 3250, 1780, 1720, 1680, 1610, 1530 cm$^{-1}$.

(6) Benzhydryl 7-[2-(2-aminothiazol-4-yl)acetamido]-3-[(E)-2-chlorovinyl]-3-cephem-4-carboxylate IR (Nujol): 3250, 1770, 1710, 1660, 1600, 1510 cm$^{-1}$.

(7) Benzhydryl 7-[2-hydroxyimino-2-(2-aminothiazol-4-yl)acetamido]-3-[(E)-2-chlorovinyl]-3-cephem-4-carboxylate (syn isomer)

IR (Nujol): 3250, 1780, 1720, 1670, 1610, 1530 cm$^{-1}$.

(8) 7-[DL-2-Hydroxy-2-(2-aminothiazol-4-yl)acetamido]-3-[(E)-2-chlorovinyl]-3-cephem-4-carboxylic acid IR (Nujol): 3270, 1760, 1670, 1630, 1520 cm$^{-1}$.

(9) 7-[2-(2-Aminothiazol-4-yl)-2-methoxycarbonylmethoxyiminoacetamido]-3-[(E)-2-chlorovinyl]-3-cephem-4-carboxylic acid (syn isomer)

IR (Nujol): 3270, 1760, 1670, 1540 cm$^{-1}$.

(10) Benzhydryl 7-(4-chloro-2-methoxycarbonylmethoxyimino-3-oxobutyramido)-3-[(E)-2-chlorovinyl]-3-cephem-4-carboxylate IR (Nujol): 3200, 1780, 1720, 1670, 1600, 1550 cm$^{-1}$.

NMR (DMSO-$d_6$, δ): 3.70 (3H, s), 3.70 (2H, m), 4.80 (2H, s), 4.97 (2H, s), 5.27 (1H, d, J=5 Hz), 5.93 (1H, dd, J=5 Hz, 8 Hz), 6.98 (1H, s), 6.98–7.67 (12H, m), 9.57 (1H, d, J=8 Hz).

(11) Benzhydryl 7-[2-(2-formamidothiazol-4-yl)-2-methoxyiminoacetamido]-3-[(E)-2-chlorovinyl]-3-cephem-4-carboxylate (syn isomer)

IR (Nujol): 3250, 1780, 1710(s), 1690, 1660, 1540 cm$^{-1}$.

NMR (DMSO-$d_6$, δ): 3.82 (2H, ABq, J=18 Hz), 3.90 (3H, s), 5.31 (1H, d, J=5 Hz), 5.95 (1H, dd, J=5 Hz, 8 Hz), 7.03 (1H, s), 7.03–7.63 (12H, m), 8.58 (1H, s), 9.84 (1H, d, J=8 Hz).

(12) Benzhydryl 7-[2-(2-aminothiazol-4-yl)-2-methoxyiminoacetamido]-3-[(E)-2-chlorovinyl]-3-cephem-4-carboxylate (syn isomer)

IR (Nujol): 3300, 1780, 1720, 1680, 1610, 1530 cm$^{-1}$.

(13) 7-[2-Methoxyimino-2-(5-amino-1,2,4-thiadiazol-3-yl)acetamido]-3-[(E)-2-chlorovinyl]-3-cephem-4-carboxylic acid (syn isomer)

IR (Nujol): 3300, 1760, 1670, 1610, 1520 cm$^{-1}$.

(14) 7-[2-Carboxymethoxyimino-2-(thiazol-4-yl)acetamido]-3-[(E)-2-chlorovinyl]-3-cephem-4-carboxylic acid (syn isomer)

IR (Nujol): 3250, 3100, 1770, 1710, 1670, 1560, 1510 cm$^{-1}$.

(15) Benzhydryl 7-[2-(t-butoxycarbonylmethoxyimino)-2-(thiazol-4-yl)acetamido]-3-[(E)-2-chlorovinyl]-3-cephem-4-carboxylate (syn isomer)

Ir (Nujol): 3270, 1780, 1740, 1720, 1680, 1650, 1550 cm$^{-1}$.

NMR (DMSO-$d_6$, δ): 1.45 (9H, s), 3.80 (2H, ABq, J=18 Hz), 4.67 (2H, broad s), 5.33 (1H, d, J=5 Hz), 5.97 (1H, dd, J=5 Hz, 8 Hz), 7.03 (1H, s), 7.03–7.70 (12H, m), 7.98 (1H, d, J=2 Hz), 9.22 (1H, d, J=2 Hz), 9.72 (1H, d, J=8 Hz).

(16) 7-[2-(2-Aminothiazol-4-yl)glyoxylamido]-3-[(E)-2-chlorovinyl]-3-cephem-4-carboxylic acid IR (Nujol): 3300, 1770, 1660, 1520 cm$^{-1}$.

(17) Benzhydryl 7-[2-(2-aminothiazol-4-yl)glyoxylamido]-3-[(E)-2-chlorovinyl]-3-cephem-4-carboxylate IR (Nujol): 3250, 1780, 1720, 1660, 1520 cm$^{-1}$.

(18) Benzhydryl 7-[2-(2-formamidothiazol-4-yl)glyoxylamido]-3-[(E)-2-chlorovinyl]-3-cephem-4-carboxylate IR (Nujol): 3150, 1780, 1720, 1690, 1670, 1510 cm$^{-1}$.

NMR (DMSO-$d_6$, δ): 3.85 (2H, ABq, J=18 Hz), 5.33 (1H, d, J=5 Hz), 5.96 (1H, dd, J=5 Hz, 8 Hz), 7.03 (1H, s), 7.10–7.67 (12H, m), 8.53 (1H, s), 8.67 (1H, s), 10.03 (1H, d, J=8 Hz), 12.70 (1H, broad s).

(19) 7-[2-(2-Aminothiazol-4-yl)acetamido]-3-[(E)-2-chlorovinyl]-3-cephem-4-carboxylic acid.

IR (Nujol): 3500, 3270, 1770, 1660, 1540 cm$^{-1}$.

(20) Benzhydryl 7-[2-((Z)-2-cyanovinylthio)acetamido]-3-[(E)-2-chlorovinyl]-3-cephem-4-carboxylate IR (Nujol): 3250, 2220, 1780, 1720, 1650, 1550 cm$^{-1}$.

NMR (DMSO-d$_6$, δ): 3.77 (2H, s), 3.77 (2H, ABq, J=18 Hz), 5.25 (1H, d, J=5 Hz), 5.72 (1H, d, J=11 Hz), 5.82 (1H, dd, J=5 Hz, 8 Hz), 7.0 (1H, s), 7.0–7.67 (13H, m), 9.28 (1H, d, J=8 Hz).

(21) 7-[2-((Z)-2-Cyanovinylthio)acetamido]-3-[(E)-2-chlorovinyl]-3-cephem-4-carboxylic acid
IR (Nujol): 3300, 2220, 1770, 1670, 1550 cm$^{-1}$.

(22) 7-[D-2-Hydroxy-2-phenylacetamido]-3-[(E)-2-chlorovinyl]-3-cephem-4-carboxylic acid
IR (Nujol): 3300, 1770, 1670, 1560, 1520 cm$^{-1}$.

(23) Benzhydryl 7-t-butoxycarbonylamino-3-[(E)-2-chlorovinyl]-3-cephem-4-carboxylate
IR (Nujol): 1775, 1730 cm$^{-1}$.

EXAMPLE 6

To a solution of benzhydryl 7-[2-t-butoxycarbonylmethoxyimino-2-(2-formamidothiazol-4-yl)acetamido]-3-[(E)-2-chlorovinyl]-3-cephem-4-carboxylate (syn isomer) (3.0 g) in a mixed solvent of methanol (30 ml) and tetrahydrofuran (5 ml) was added concentrated hydrochloric acid (1.67 ml) at room temperature, and the mixture was stirred for two hours at the same temperature. The reaction mixture was diluted with water (40 ml), adjusted to pH 6.0 with an aqueous solution of sodium bicarbonate and extracted with ethyl acetate. The extract was washed with a saturated aqueous solution of sodium chloride, dried and evaporated under reduced pressure. The residue was triturated with diisopropyl ether and collected by filtration to give benzhydryl 7-[2-t-butoxycarbonylmethoxyimino-2-(2-aminothiazol-4-yl)acetamido]-3-[(E)-2-chlorovinyl]-3-cephem-4-carboxylate (syn isomer) (2.6 g).
IR (Nujol): 3250, 1780, 1720, 1680, 1610, 1530 cm$^{-1}$.
NMR (DMSO-d$_6$, δ): 1.40 (9H, s), 3.75 (2H, broad s), 4.57 (2H, s), 5.28 (1H, d, J=5 Hz), 5.92 (1H, dd, J=5 Hz, 8 Hz), 6.82 (1H, s), 6.98 (1H, s), 6.95–7.57 (12H, m).

EXAMPLE 7

The following compounds were obtained according to a similar manner to that of Example 6.

(1) 7-[2-Carboxymethoxyimino-2-(2-aminothiazol-4-yl)acetamido]-3-[(E)-2-chlorovinyl]-3-cephem-4-carboxylic acid (syn isomer)
IR (nujol): 3250, 1770, 1670, 1630, 1560 cm$^{-1}$.

(2) Benzhydryl 7-[2-methoxyimino-2-(5-amino-1,2,4-thiadiazol-3-yl)acetamido]-3-[(E)-2-chlorovinyl]-3-cephem-4-carboxylate (syn isomer)
IR (Nujol): 3300, 1770, 1720, 1670, 1610 cm$^{-1}$.

(3) 7-[2-Methoxyimino-2-(2-aminothiazol-4-yl)acetamido]-3-[(E)-2-chlorovinyl]-3-cephem-4-carboxylic acid (syn isomer)
IR (Nujol): 3270, 1770, 1670, 1550 (broad) cm$^{-1}$.

(4) 7-[2-Hydroxyimino-2-(2-aminothiazol-4-yl)acetamido]-3-[(E)-2-chlorovinyl]-3-cephem-4-carboxylic acid (syn isomer)
IR (Nujol): 3300, 1760, 1670(s), 1635, 1560 cm$^{-1}$.

(5) Benzhydryl 7-[2-methoxycarbonylmethoxyimino-2-(2-aminothiazol-4-yl)acetamido]-3-[(E)-2-chlorovinyl]-3-cephem-4-carboxylate (syn isomer)
IR (Nujol): 3250, 1780, 1720, 1680, 1610, 1530 cm$^{-1}$.

(6) Benzhydryl 7-[2-(2-aminothiazol-4-yl)acetamido]-3-[(E)-2-chlorovinyl]-3-cephem-4-carboxylate
IR (Nujol): 3250, 1770, 1710, 1660, 1600, 1510 cm$^{-1}$.

(7) Benzhydryl 7-[2-hydroxyimino-2-(2-aminothiazol-4-yl)acetamido]-3-[(E)-2-chlorovinyl]-3-cephem-4-carboxylate (syn isomer)
IR (nujol): 3250, 1780, 1720, 1670, 1610, 1530 cm$^{-1}$.

(8) 7-[DL-2-Hydroxy-2-(2-aminothiazol-4-yl)acetamido]-3-[(E)-2-chlorovinyl]-3-cephem-4-carboxylic acid
IR (Nujol): 3270, 1760, 1670, 1630, 1520 cm$^{-1}$.

(9) 7-[2-(2-Aminothiazol-4-yl)-2-methoxycarbonylmethoxyiminoacetamido]-3-[(E)-2-chlorovinyl]-3-cephem-4-carboxylic acid (syn isomer).
IR (Nujol): 3270, 1760, 1670, 1540 cm$^{-1}$.

(10) Benzhydryl 7-[2-(2-aminothiazol-4-yl)-2-methoxyiminoacetamido]-3-[(E)-2-chlorovinyl]-3-cephem-4-carboxylate (syn isomer)
IR (Nujol): 3300, 1780, 1720, 1680, 1610, 1530 cm$^{-1}$.
NMR (DMSO-d$_6$, δ): 3.77 (2H, ABq, J=18 Hz), 3.87 (3H, s), 5.30 (1H, dd, J=5 Hz), 5.93 (1H, dd, J=5 Hz, 8 Hz), 6.82 (1H, s), 7.03 (1H, s), 7.03–7.67 (12H, m), 9.75 (1H, d, J=8 Hz).

(11) 7-[2-Methoxyimino-2-(5-amino-1,2,4-thiadiazol-3-yl)acetamido]-3-[(E)-2-chlorovinyl]-3-cephem-4-carboxylic acid (syn isomer)
IR (Nujol): 3300, 1760, 1670, 1610, 1520 cm$^{-1}$.

(12) 7-[2-(2-Aminothiazol-4-yl)glyoxylamido]-3-[(E)-2-chlorovinyl]-3-cephem-4-carboxylic acid
IR (Nujol): 3300, 1770, 1660, 1520 cm$^{-1}$.

(13) Benzhydryl 7-[2-(2-aminothiazol-4-yl)glyoxylamido]-3-[(E)-2-chlorovinyl]-3-cephem-4-carboxylate
IR (Nujol): 3250, 1780, 1720, 1660, 1520 cm$^{-1}$.
NMR (DMSO-d$_6$, δ): 3.85 (2H, broad s), 5.32 (1H, d, J=5 Hz), 5.83 (1H, dd, J=5 Hz, 8 Hz), 7.02 (1H, s), 7.05 (1H, s), 7.0–7.7 (12H, m), 9.88 (1H, dd, J=8 Hz).

(14) 7-[2-(2-Aminothiazol-4-yl)acetamido]-3-[(E)-2-chlorovinyl]-3-cephem-4-carboxylic acid
IR (Nujol): 3500, 3270, 1770, 1660, 1540 cm$^{-1}$.

EXAMPLE 8

To a mixture of benzhydryl 7-[2-t-butoxycarbonylmethoxyimino-2-(2-aminothiazol-4-yl)acetamido]-3-[(E)-2-chlorovinyl]-3-cephem-4-carboxylate (syn isomer) (2.2 g) and anisole (2.2 ml) was added trifluoroacetic acid (9.0 ml) in an ice-bath. The mixture was stirred for two hours at room temperature and poured into diisopropyl ether (180 ml). The resulting precipitates were collected by filtration and washed with diisopropyl ether. The precipitates were dissolved in an aqueous solution of sodium bicarbonate and washed with ethyl acetate. The aqueous layer was concentrated to remove organic solvent under reduced pressure, cooled to 5° C. and adjusted to pH 2.2 with diluted hydrochloric acid. The resulting precipitates were collected by filtration, washed with water and dried in vacuo to give 7-[2-carboxymethoxyimino-2-(2-aminothiazol-4-yl)acetamido]-3-[(E)-2-chlorovinyl]-3-cephem-4-carboxylic acid (syn isomer) (1.07 g).
IR (Nujol): 3250, 1770, 1670, 1630, 1560 cm$^{-1}$.
NMR (DMSO-d$_6$, δ): 3.75 (2H, broad s), 4.65 (2H, s), 5.28 (1H, d, J=5 Hz), 5.87 (1H, dd, J=5 Hz, 8 Hz), 6.83 (1H, s), 6.92 (1H, d, J=14 Hz), 7.22 (1H, d, J=14 Hz), 9.57 (1H, d, J=8 Hz).

EXAMPLE 9

The following compound was obtained according to a similar manner to that of Example 8.

7-[2-Carboxymethoxyimino-2-(thiazol-4-yl)acetamido]-3-[(E)-2-chlorovinyl]-3-cephem-4-carboxylic acid (syn isomer)
IR (Nujol): 3250, 3100, 1770, 1710, 1670, 1560, 1510 cm$^{-1}$.

NMR (DMSO-d$_6$, δ): 3.65 (2H, ABq, J=18 Hz), 4.68 (2H, broad(s), 5.13 (1H, d, J=5 Hz), 5.77 (1H, dd, J=5 Hz, 8 Hz), 6.76 (1H, d, J=14 Hz), 6.90 (1H, d, J=14 Hz), 7.78 (1H, d, J=2 Hz), 8.96 (1H, d, J=2 Hz), 9.43 (1H, d, J=8 Hz).

EXAMPLE 10

Trifluoroacetic acid (6 ml) was added to a solution of benzhydryl 7-[2-(2-aminothiazol-4-yl)-2-methoxyiminoacetamido]-3-[(E)-2-chlorovinyl]-3-cephem-4-carboxylate (syn isomer) (1.4 g) in methylene chloride (4 ml) and anisole (1.4 ml) under ice-cooling and the mixture was stirred at the same temperature for 40 minutes. The resulting solution was added dropwise to diisopropyl ether (200 ml) and the resultant precipitates were collected by filtration. The precipitates were added to a mixture of water (30 ml) and ethyl acetate (30 ml) and the solution was adjusted to pH 7.0 with 5% aqueous solution of sodium bicarbonate. The separated aqueous layer was adjusted to pH 2.7 with 10% hydrochloric acid and extracted with ethyl acetate. The extract was washed with brine, dried over magnesium sulfate and evaporated under reduced pressure to give 7-[2-methoxyimino-2-(2-aminothiazol-4-yl)acetamido]-3-[(E)-2-chlorovinyl]-3-cephem-4-carboxylic acid (syn isomer) (0.66 g).

IR (Nujol): 3270, 1770, 1670, 1550 (broad) cm$^{-1}$.

NMR (DMSO-d$_6$, δ): 3.63 (2H, ABq, J=18 Hz), 3.77 (3H, s), 5.08 (1H, d, J=5 Hz), 5.65 (1H, dd, J=5 Hz, 8 Hz), 6.63 (1H, s), 6.76 (1H, d, J=14 Hz), 6.98 (1H, d, J=14 Hz), 9.42 (1H, d, J=8 Hz).

EXAMPLE 11

To a solution of benzhydryl 7-[2-(2-aminothiazol-4-yl)-2-hydroxyiminoacetamido]-3-[(E)-2-chlorovinyl]-3-cephem-4-carboxylate (syn isomer) (2.5 g) in a mixture of acetic acid (2.5 ml) and anisole (9.6 ml) was dropwise added boron trifluoride etherate (2.5 ml) at 3° C. and the mixture was stirred for 30 minutes at the same temperature for 30 minutes. The reaction mixture was dissolved in 20% aqueous solution of potassium carbonate, washed with ethyl acetate, concentrated to remove the organic solvent under reduced pressure, cooled to 5° C. and adjusted to pH 2.3 with 10% hydrochloric acid. The resultant precipitates were collected by filtration, washed with water and dried in vacuo to give 7-[2-hydroxyimino-2-(2-aminothiazol-4-yl)acetamido]-3-[(E)-2-chlorovinyl]-3-cephem-4-carboxylic acid (syn isomer) (2.65 g)

IR (Nujol): 3300, 1760, 1670(s), 1635, 1560 cm$^{-1}$.

NMR (DMSO-d$_6$, δ): 3.65 (2H, ABq, J=18 Hz), 5.12 (1H, d, J=5 Hz), 5.67 (1H, dd, J=5 Hz, 8 Hz), 6.67 (1H, s), 6.78 (1H, d, J=14 Hz), 7.00 (1H, d, J=14 Hz), 9.45 (1H, d, J=8 Hz), 12.00 (1H, broad s).

EXAMPLE 12

The following compounds were obtained according to similar manners to those of Examples 10 and 11.

(1) 7-[2-Carboxymethoxyimino-2-(2-aminothiazol-4-yl)acetamido]-3-[(E)-2-chlorovinyl]-3-cephem-4-carboxylic acid (syn isomer).

IR (Nujol): 3250, 1770, 1670, 1630, 1560 cm$^{-1}$.

(2) 7-[DL-2-Hydroxy-2-(2-aminothiazol-4-yl)acetamido]-3-[(E)-2-chlorovinyl]-3-cephem-4-carboxylic acid.

IR (Nujol): 3270, 1760, 1670, 1630, 1520 cm$^{-1}$.

(3) 7-[2-(2-Aminothiazol-4-yl)-2-methoxycarbonylmethoxyiminoacetamido]-3-[(E)-2-chlorovinyl]-3-cephem-4-carboxylic acid (syn isomer).

IR (Nujol): 3270, 1760, 1670, 1540 cm$^{-1}$.

NMR (DMSO-d$_6$, δ): 3.68 (3H, s), 3.68 (2H, m), 4.72 (2H, broad s), 5.23 (1H, d, J=5 Hz), 5.83 (1H, dd, J=5 Hz, 8 Hz), 6.83 (1H, s), 6.93 (1H, d, J=4 Hz), 7.20 (1H, d, J=14 Hz), 9.60 (1H, d, J=8 Hz).

(4) 7-[2-Methoxyimino-2-(5-amino-1,2,4-thiadiazol-3-yl)acetamido]-3-[(E)-2-chlorovinyl]-3-cephem-4-carboxylic acid (syn isomer)

IR (Nujol): 3300, 1760, 1670, 1610, 1520 cm$^{-1}$.

NMR (DMSO-d$_6$, δ): 3.64 (2H, ABq, J=18 Hz), 3.83 (3H, s), 5.05 (1H, d, J=5 Hz), 5.68 (1H, dd, J=5 Hz, 8 Hz), 6.75 (1H, d, J=14 Hz), 7.96 (2H, broad s), 7.97 (1H, d, J=14 Hz), 9.38 (1H, d, J=8 Hz).

(5) 7-[2-Carboxymethoxyimino-2-(thiazol-4-yl)acetamido]-3-[(E)-2-chlorovinyl]-3-cephem-4-carboxylic acid (syn isomer)

IR (Nujol): 3250, 3100, 1770, 1710, 1670, 1560, 1510 cm$^{-1}$.

(6) 7-[2-(2-Aminothiazol-4-yl)glyoxylamido]-3-[(E)-2-chlorovinyl]-3-cephem-4-carboxylic acid IR (Nujol): 3300, 1770, 1660, 1520 cm$^{-1}$.

NMR (DMSO-d$_6$, δ): 3.77 (2H, broad s), 5.23 (1H, d, J=5 Hz), 5.80 (1H, dd, J=5 Hz, 8 Hz), 6.97 (1H, d, J=14 Hz), 7.27 (1H, d, J=14 Hz), 9.82 (1H, d, J=8 Hz).

(7) 7-[2-(2-Aminothiazol-4-yl)acetamido]-3-[(E)-2-chlorovinyl]-3-cephem-4-carboxylic acid IR (Nujol): 3500, 3270, 1770, 1660, 1540 cm$^{-1}$.

NMR (DMSO-d$_6$, δ): 3.32 (2H, broad s), 3.65 (2H, ABq, J=18 Hz), 5.03 (1H, d, J=5 Hz), 5.58 (1H, dd, J=5 Hz, 8 Hz), 6.13 (1H, s), 6.77 (1H, d, J=14 Hz), 6.77 (2H, broad s), 7.0 (1H, d, J=14 Hz), 8.70 (1H, d, J=8 Hz).

(8) 7-[2-((Z)-2-Cyanovinylthio)acetamido]-3-[(E)-2-chlorovinyl]-3-cephem-4-carboxylic acid IR (Nujol): 3300, 2220, 1770, 1670, 1550 cm$^{-1}$.

NMR (DMSO-d$_6$, δ): 3.63 (2H, s), 3.63 (2H, ABq, J=18 Hz), 5.05 (1H, d, J=5 Hz), 5.60 (1H, dd, J=5 Hz, 8 Hz), 5.57 (1H, d, J=11 Hz), 6.77 (1H, d, J=14 Hz), 6.98 (1H, d, J=14 Hz), 7.48 (1H, d, J=14 Hz), 9.00 (1H, d, J=8 Hz).

(9) 7-[D-2-Hydroxy-2-phenylacetamido]-3-[(E)-2-chlorovinyl]-3-cephem-4-carboxylic acid IR (Nujol): 3300, 1770, 1670, 1560, 1520 cm$^{-1}$.

NMR (DMSO-d$_6$, δ): 3.62 (2H, ABq, J=18 Hz), 4.98 (1H, broad s), 5.02 (1H, d, J=5 Hz), 5.58 (1H, dd, J=5 Hz, 8 Hz), 6.75 (1H, d, J=14 Hz), 6.98 (1H, dd, J=14 Hz), 7.0–7.40 (5H, m), 9.55 (1H, d, J=8 Hz).

EXAMPLE 13

To a solution of benzhydryl 7-(4-chloro-2-methoxycarbonylmethoxyimino-3-oxobutyramido)-3-[(E)-2-chlorovinyl]-3-cephem-4-carboxylate (1.65 g) in a mixture of tetrahydrofuran (10 ml) and water (10 ml) were added thiourea (0.39 g) and sodium acetate (1.05 g). The mixture was stirred at ambient temperature for 2 hours and extracted with ethyl acetate. The extract was washed with a saturated aqueous solution of sodium chloride and dried over magnesium sulfate, and the solvent was evaporated under reduced pressure. The residue was triturated with diisopropyl ether and collected by filtration to give benzhydryl 7-[2-methoxycarbonylmethoxyimino-2-(2-aminothiazol-4-yl)acetamido]-3-[(E)-2-chlorovinyl]-3-cephem-4-carboxylate (syn isomer) (1.45 g).

IR (Nujol): 3250, 1780, 1720, 1680, 1610, 1530 cm$^{-1}$.

NMR (DMSO-d$_6$, δ): 3.67 (3H, s), 3.67 (2H, m), 4.72 (2H, broad s), 5.28 (1H, d, J=5 Hz), 5.93 (1H, dd, J=5 Hz, 8 Hz), 6.85 (1H, s), 7.00 (1H, s), 7.0–7.73 (12H, m), 9.67 (1H, d, J=8 Hz).

EXAMPLE 14

To a solution of benzhydryl 7-(4-bromo-3-oxobutyramido)-3-[(E)-2-chlorovinyl]-3-cephem-4-carboxylate (1.2 g) in a mixture of tetrahydrofuran (15 ml) and ethyl alcohol (15 ml) was added thiourea (0.46 g). The mixture was stirred for an hour at 30° C., poured into an aqueous solution of sodium bicarbonate and extracted with ethyl acetate. The extract was washed with 10% aqueous solution of sodium chloride and dried over magnesium sulfate. The solvent was evaporated under reduced pressure, and the residue was triturated with diisopropyl ether and collected by filtration to give benzhydryl 7-[2-(2-aminothiazol-4-yl)acetamido]-3-[(E)-2-chlorovinyl]-3-cephem-4-carboxylate (0.83 g).

IR (Nujol): 3250, 1770, 1710, 1660, 1600, 1510 cm$^{-1}$.
NMR (DMSO-d$_6$, δ): 3.45 (2H, ABq, J=18 Hz), 5.27 (1H, d, J=5 Hz), 5.67 (1H, dd, J=5 Hz, 8 Hz), 6.33 (1H, s), 7.0 (1H, s), 7.0–7.67 (12H, m), 8.97 (1H, d, J=8 Hz).

EXAMPLE 15

The following compounds were obtained according to similar manners to those of Examples 13 and 14.

(1) Benzhydryl 7-[2-t-butoxycarbonylmethoxyimino-2-(2-formamidothiazol-4-yl)acetamido]-3-[(E)-2-chlorovinyl]-3-cephem-4-carboxylate (syn isomer)
IR (Nujol): 3150, 1785, 1720, 1680, 1540 cm$^{-1}$.

(2) Benzhydryl 7-[2-t-butoxycarbonylmethoxyimino-2-(2-aminothiazol-4-yl)acetamido]-3-[(E)-2-chlorovinyl]-3-cephem-4-carboxylate (syn isomer)
IR (Nujol): 3250, 1780, 1720, 1680, 1610, 1530 cm$^{-1}$.

(3) 7-[2-Carboxymethoxyimino-2-(2-aminothiazol-4-yl)acetamido]-3-[(E)-2-chlorovinyl]-3-cephem-4-carboxylic acid (syn isomer)
IR (Nujol): 3250, 1770, 1670, 1630, 1560 cm$^{-1}$.

(4) 7-[2-Methoxyimino-2-(2-aminothiazol-4-yl)acetamido]-3-[(E)-2-chlorovinyl]-3-cephem-4-carboxylic acid (syn isomer)
IR (Nujol): 3270, 1770, 1670, 1550 (broad) cm$^{-1}$.

(5) 7-[2-Hydroxyimino-2-(2-aminothiazol-4-yl)acetamido]-3-[(E)-2-chlorovinyl]-3-cephem-4-carboxylic acid (syn isomer)
IR (Nujol): 3300, 1760, 1670(s), 1635, 1560 cm$^{-1}$.

(6) 7-[2-(2-Aminothiazol-4-yl)-2-methoxycarbonylmethoxyiminoacetamido]-3-[(E)-2-chlorovinyl]-3-cephem-4-carboxylic acid (syn isomer)
IR (Nujol): 3270, 1760, 1670, 1540 cm$^{-1}$.

(7) Benzhydryl 7-[2-(2-formamidothiazol-4-yl)-2-methoxyiminoacetamido]-3-[(E)-2-chlorovinyl]-3-cephem-4-carboxylate (syn isomer)
IR (Nujol): 3250, 1780, 1710(s), 1690, 1660, 1540 cm$^{-1}$.

(8) Benzhydryl 7-[2-(2-aminothiazol-4-yl)-2-methoxyiminoacetamido]-3-[(E)-2-chlorovinyl]-3-cephem-4-carboxylate (syn isomer)
IR (Nujol): 3300, 1780, 1720, 1680, 1610, 1530 cm$^{-1}$.

(9) 7-[2-(2-Aminothiazol-4-yl)glyoxylamido]-3-[(E)-2-chlorovinyl]-3-cephem-4-carboxylic acid
IR (Nujol): 3300, 1770, 1660, 1520 cm$^{-1}$.

(10) Benzhydryl 7-[2-(2-aminothiazol-4-yl)glyoxylamido]-3-[(E)-2-chlorovinyl]-3-cephem-4-carboxylate
IR (Nujol): 3250, 1780, 1720, 1660, 1520 cm$^{-1}$.

(11) Benzhydryl 7-[2-(2-formamidothiazol-4-yl)glyoxylamido]-3-[(E)-2-chlorovinyl]-3-cephem-4-carboxylate
IR (Nujol): 3150, 1780, 1720, 1690, 1670, 1510 cm$^{-1}$.

(12) 7-[2-(2-Aminothiazol-4-yl)acetamido]-3-[(E)-2-chlorovinyl]-3-cephem-4-carboxylic acid
IR (Nujol): 3500, 3270, 1770, 1660, 1540 cm$^{-1}$.

EXAMPLE 16

To a solution of benzhydryl 7-(4-bromo-3-oxobutyramido)-3-[(E)-2-chlorovinyl]-3-cephem-4-carboxylate (3.5 g) in a mixture of methylene chloride (32 ml) and acetic acid (12 ml) was dropwise added an aqueous solution (3 ml) of sodium nitrite (0.61 g) at −22° C. and the mixture was stirred for 6 minutes at the same temperature to give a reaction mixture containing benzhydryl 7-(4-bromo-2-hydroxyimino-3-oxobutyramido)-3-[(E)-2-chlorovinyl]-3-cephem-4-carboxylate. To the reaction mixture was added ethyl acetate (0.77 g). The mixture was stirred for 5 minutes at −20° C. and washed with water and 10% aqueous solution of sodium chloride successively, and a mixture of thiourea (0.54 g) and N,N-dimethylacetamide (7.0 ml) was added thereto at 36° C. The mixture was evaporated to remove methylene chloride. The residue was dissolved in ethyl acetate, washed with water and dried over magnesium sulfate. The solvent was evaporated under reduced pressure and the residue was triturated with diisopropyl ether and collected by filtration to give benzhydryl 7-[2-hydroxyimino-2-(2-aminothiazol-4-yl)acetamido]-3-[(E)-2-chlorovinyl]-3-cephem-4-carboxylate (syn isomer) (2.65 g).

IR (Nujol): 3250, 1780, 1720, 1670, 1610, 1530 cm$^{-1}$.
NMR (DMSO-d$_6$, δ): 3.78 (2H, ABq, J=18 Hz), 5.30 (1H, d, J=5 Hz), 5.97 (1H, dd, J=5 Hz, 8 Hz), 6.73 (1H, s), 7.00 (1H, s), 7.0–7.70 (12H, m), 9.53 (1H, d, J=8 Hz), 11.30 (1H, broad s).

EXAMPLE 17

Sodium borohydride (0.064 g) was added to a suspension of 7-[2-(2-aminothiazol-4-yl)glyoxylamido]-3-[(E)-2-chlorovinyl]-3-cephem-4-carboxylic acid (0.7 g) in methanol (10 ml) under ice-cooling, and the mixture was stirred for an hour at the same temperature and evaporated under reduced pressure. The residue was dissolved in water and the solution was adjusted to pH 2.7 with 10% hydrochloric acid. The resultant precipitates were collected, washed with water and dried in vacuo to give 7-[DL-2-hydroxy-2-(2-aminothiazol-4-yl)acetamido]-3-[(E)-2-chlorovinyl]-3-cephem-4-carboxylic acid (0.5 g).

IR (Nujol): 3270, 1760, 1670, 1630, 1520 cm$^{-1}$.
NMR (DMSO-d$_6$, δ): 3.65 (2H, m), 3.80 (1H, s), 5.07 (1H, d, J=5 Hz), 5.58 (1H, dd, J=5 Hz, 8 Hz), 6.34 (1H, s), 6.77 (1H, d, J=14 Hz), 7.0 (1H, d, J=14 Hz), 8.28 (1H, m).

EXAMPLE 18

To a solution of benzhydryl 7-t-butoxycarbonylamino-3-[(E)-2-chlorovinyl]-3-cephem-4-carboxylate-1-oxide (7.3 g) in N,N-dimethylformamide (35 ml) was added phosphorus trichloride (1.76 ml) at −40° C. After stirring at the same temperature for 30 minutes, the mixture was poured into ice-water. The resulting precipitate was collected by filtration and dried to give benzhydryl 7-t-butoxycarbonylamino-3-[(E)-2-chlorovinyl]-3-cephem-4-carboxylate (6.3 g).

IR (Nujol): 1775, 1730 cm$^{-1}$.

NMR (DMSO-d$_6$, δ): 1.45 (9H, s), 3.77 (2H, m), 5.15 (1H, d, J=5 Hz), 5.50 (1H, dd, J=5 Hz, 8 Hz), 6.8–7.4 (2H, m), 7.0 (1H, s), 7.50 (10H, m), 7.95 (1H, d, J=8 Hz).

EXAMPLE 19

The following compounds were obtained according to a similar manner to that of Example 18.

(1) Benzhydryl 7-[2-t-butoxycarbonylmethoxyimino-2-(2-formamidothiazol-4-yl)acetamido]-3-[(E)-2-chlorovinyl]-3-cephem-4-carboxylate (syn isomer)
IR (Nujol): 3150, 1785, 1720, 1680, 1540 cm$^{-1}$.

(2) Benzhydryl 7-[2-methoxyimino-2-(5-amino-1,2,4-thiadiazol-3-yl)acetamido]-3-[(E)-2-chlorovinyl]-3-cephem-4-carboxylate (syn isomer)
IR (Nujol): 3300, 1770, 1720, 1670, 1610 cm$^{-1}$.

(3) Benzhydryl 7-(4-bromo-3-oxobutyramido)-3-[(E)-2-chlorovinyl]-3-cephem-4-carboxylate
IR (Nujol): 3300, 1775, 1720, 1660, 1530 cm$^1$.

(4) Benzhydryl 7-[D-2-hydroxy-2-phenylacetamido]-3-[(E)-2-chlorovinyl]-3-cephem-4-carboxylate
IR (Nujol): 3350, 1780, 1720, 1675, 1560, 1510 cm$^{-1}$.

(5) Benzhydryl 7-[2-t-butoxycarbonylmethoxyimino-2-(2-aminothiazol-4-yl)acetamido]-3-[(E)-2-chlorovinyl]-3-cephem-4-carboxylate (syn isomer).
IR (Nujol): 3250, 1780, 1720, 1680, 1610, 1530 cm$^{-1}$.

(6) 7-[2-Carboxymethoxyimino-2-(2-aminothiazol-4-yl)acetamido]-3-[(E)-2-chlorovinyl]-3-cephem-4-carboxylic acid (syn isomer).
IR (Nujol): 3250, 1770, 1670, 1630, 1560 cm$^{-1}$.

(7) 7-[2-Methoxyimino-2-(2-aminothiazol-4-yl)acetamido]-3-[(E)-2-chlorovinyl]-3-cephem-4-carboxylic acid (syn isomer)
IR (Nujol): 3270, 1770, 1670, 1550 (broad) cm$^{-1}$.

(8) 7-[2-Hydroxyimino-2-(2-aminothiazol-4-yl)acetamido]-3-[(E)-2-chlorovinyl]-3-cephem-4-carboxylic acid (syn isomer)
IR (Nujol): 3300, 1760, 1670(s), 1635, 1500 cm$^{-1}$.

(9) Benzhydryl 7-[2-methoxycarbonylmethoxyimino-2-(2-aminothiazol-4-yl)acetamido]-3-[(E)-2-chlorovinyl]-3-cephem-4-carboxylate (syn isomer).
IR (Nujol): 3250, 1780, 1720, 1680, 1610, 1530 cm$^{-1}$.

(10) Benzhydryl 7-[2-(2-aminothiazol-4-yl)acetamido]-3-[(E)-2-chlorovinyl]-3-cephem-4-carboxylate.
IR (Nujol): 3250, 1770, 1710, 1660, 1600, 1510 cm$^{-1}$.

(11) Benzhydryl 7-[2-hydroxyimino-2-(2-aminothiazol-4-yl)acetamido]-3-[(E)-2-chlorovinyl]-3-cephem-4-carboxylate (syn isomer)
IR (Nujol): 3250, 1780, 1720, 1670, 1610, 1530 cm$^{-1}$.

(12) 7-[DL-2-Hydroxy-2-(2-aminothiazol-4-yl)acetamido]-3-[(E)-2-chlorovinyl]-3-cephem-4-carboxylic acid
IR (Nujol): 3270, 1760, 1670, 1630, 1520 cm$^{-1}$.

(13) 7-[2-(2-Aminothiazol-4-yl)-2-methoxycarbonylmethoxyiminoacetamido]-3-[(E)-2-chlorovinyl]-3-cephem-4-carboxylic acid (syn isomer)
IR (Nujol): 3270, 1760, 1670, 1540 cm$^{-1}$.

(14) Benzhydryl 7-(4-chloro-2-methoxycarbonylmethoxyimino-3-oxobutyramido)-3-[(E)-2-chlorovinyl]-3-cephem-4-carboxylate
IR (Nujol): 3200, 1780, 1720, 1670, 1600, 1550 cm$^{-1}$.

(15) Benzhydryl 7-[2-(2-formamidothiazol-4-yl)-2-methoxyiminoacetamido]-3-[(E)-2-chlorovinyl]-3-cephem-4-carboxylate (syn isomer)
IR (Nujol): 3250, 1780, 1710(s), 1690, 1660, 1540 cm$^{-1}$.

(16) Benzhydryl 7-[2-(2-aminothiazol-4-yl)-2-methoxyiminoacetamido]-3-[(E)-2-chlorovinyl]-3-cephem-4-carboxylate (syn isomer)
IR (Nujol): 3300, 1780, 1720, 1680, 1610, 1530 cm$^{-1}$.

(17) 7-[2-Methoxyimino-2-(5-amino-1,2,4-thiadiazol-3-yl)acetamido]-3-[(E)-2-chlorovinyl]-3-cephem-4-carboxylic acid (syn isomer)
IR (Nujol): 3300, 1760, 1670, 1610, 1520 cm$^{-1}$.

(18) 7-[2-Carboxymethoxyimino-2-(thiazol-4-yl)acetamido]-3-[(E)-2-chlorovinyl]-3-cephem-4-carboxylic acid (syn isomer)
IR (Nujol): 3250, 3100, 1770, 1710, 1670, 1560, 1510 cm$^{-1}$.

(19) Benzhydryl 7-[2-(t-butoxycarbonylmethoxyimino)-2-(thiazol-4-yl)acetamido]-3-[(E)-2-chlorovinyl]-3-cephem-4-carboxylate (syn isomer)
IR (Nujol): 3270, 1780, 1740, 1720, 1680, 1650, 1550 cm$^{-1}$.

(20) 7-[2-(2-Aminothiazol-4-yl)glyoxylamido]-3-[(E)-2-chlorovinyl]-3-cephem-4-carboxylic acid
IR (Nujol): 3300, 1770, 1660, 1520 cm$^{-1}$.

(21) Benzhydryl 7-[2-(2-aminothiazol-4-yl)glyoxylamido]-3-[(E)-2-chlorovinyl]-3-cephem-4-carboxylate
IR (Nujol): 3250, 1780, 1720, 1660, 1520 cm$^{-1}$.

(22) Benzhydryl 7-[2-(2-formamidothiazol-4-yl)glyoxylamido]-3-[(E)-2-chlorovinyl]-3-cephem-4-carboxylate
IR (Nujol): 3150, 1780, 1720, 1690, 1670, 1510 cm$^{-1}$.

(23) 7-[2-(2-Aminothiazol-4-yl)acetamido]-3-[(E)-2-chlorovinyl]-3-cephem-4-carboxylic acid
IR (Nujol): 3500, 3270, 1770, 1660, 1540 cm$^{-1}$.

(24) Benzhydryl 7-[2-((Z)-2-cyanovinylthio)acetamido]-3-[(E)-2-chlorovinyl]-3-cephem-4-carboxylate
IR (Nujol): 3250, 2220, 1780, 1720, 1650, 1550 cm$^{-1}$.

(25) 7-[2-((Z)-2-Cyanovinylthio)acetamido]-3-[(E)-2-chlorovinyl]-3-cephem-4-carboxylic acid
IR (Nujol): 3300, 2220, 1770, 1670, 1550 cm$^{-1}$.

(26) 7-[D-2-Hydroxy-2-phenylacetamido]-3-[(E)-2-chlorovinyl]-3-cephem-4-carboxylic acid
IR (Nujol): 3300, 1770, 1670, 1500, 1520 cm$^{-1}$.

(27) Benzhydryl 7-amino-3-[(E)-2-chlorovinyl]-3-cephem-4-carboxylate
IR (Nujol): 3350, 1775, 1725 cm$^{-1}$.

EXAMPLE 20

To a solution of benzhydryl 7-t-butoxycarbonylamino-3-[(E)-2-chlorovinyl]-3-cephem-4-carboxylate (5.0 g) in acetonitrile (50 ml) was added p-toluenesulfonic acid monohydrate (3.23 g). After stirring at 35° C. for 50 minutes, the mixture was poured into a saturated aqueous solution of sodium chloride, adjusted to pH 7.5 with 5% aqueous solution of sodium bicarbonate and extracted with ethyl acetate. The extract was washed with a saturated aqueous solution of sodium chloride, dried over magnesium sulfate and concentrated under reduced pressure. The residue as triturated with n-hexane to give benzhydryl 7-amino-3-[(E)-2-chlorovinyl]-3-cephem-4-carboxylate (2.50 g)
IR (Nujol): 3350, 1775, 1725 cm$^{-1}$.
NMR (DMSO-d$_6$, δ): 3.50, 3.80 (2H, ABq, J=20 Hz), 4.78, 4.98 (2H, ABq, J=5 Hz), 6.79 (1H, s), 6.8–7.5 (14H, m).

What we claim is:
1. 7-[2-carboxymethoxyimino-2-(2-aminothiazol-4-yl)acetamido]-3-[2-chlorovinyl]-3-cephem-4-carboxylic acid (syn isomer) and pharmaceutically acceptable salts thereof.

2. A method of treating an infectious disease comprising administering to a subject in need of such treatment an antimicrobially effective amount of the compound of claim 1.

3. A pharmaceutical antimicrobial composition comprising an antimicrobially effective amount of a compound of claim 1 or pharmaceutically acceptable salt thereof in association with a pharmaceutically acceptable, substantially non-toxic carrier or excipient.

* * * * *